United States Patent
Monsalve

(10) Patent No.: US 11,499,952 B2
(45) Date of Patent: Nov. 15, 2022

(54) PROCESS FOR QUANTIFICATION OF METAL AMINO ACID CHELATES IN SOLUTIONS AND SOLIDS

(71) Applicant: Premex, Inc., Durham, NC (US)

(72) Inventor: Paula Leon Monsalve, Medellin (CO)

(73) Assignee: PREMEX, INC., Durham, NC (US)

( * ) Notice: Subject to any disclaimer, the term of this patent is extended or adjusted under 35 U.S.C. 154(b) by 395 days.

(21) Appl. No.: 16/408,628

(22) Filed: May 10, 2019

(65) Prior Publication Data

US 2019/0346413 A1    Nov. 14, 2019

Related U.S. Application Data

(60) Provisional application No. 62/670,202, filed on May 11, 2018.

(51) Int. Cl.

| | | |
|---|---|---|
| *G01N 31/02* | (2006.01) | |
| *G01N 23/207* | (2018.01) | |
| *G01N 30/02* | (2006.01) | |
| *G01N 23/2055* | (2018.01) | |

(52) U.S. Cl.
CPC .......... *G01N 31/02* (2013.01); *G01N 23/207* (2013.01); *G01N 23/2055* (2013.01); *G01N 30/02* (2013.01); *G01N 2030/027* (2013.01); *G01N 2223/618* (2013.01)

(58) Field of Classification Search
CPC ...... G01N 31/02; G01N 23/207; G01N 30/02; G01N 23/2055; G01N 2030/027; G01N 2223/618; G01N 2223/0566; G01N 2223/1016; G01N 33/02; G01N 2030/884; H01J 37/32972

See application file for complete search history.

(56) References Cited

U.S. PATENT DOCUMENTS

| | | | | |
|---|---|---|---|---|
| 7,144,737 B2* | 12/2006 | Hartle | ............... | G01N 21/3563 436/86 |
| 7,589,235 B2* | 9/2009 | Christgau | ............... | A61P 19/08 562/590 |
| 7,989,435 B2* | 8/2011 | Coppolino | ............... | C07F 9/093 514/102 |
| 2008/0248583 A1* | 10/2008 | Ericson | ............... | G01N 21/6428 436/76 |
| 2013/0077754 A1* | 3/2013 | Sasaki | ............... | G01N 23/20 378/71 |

FOREIGN PATENT DOCUMENTS

| | | | | |
|---|---|---|---|---|
| WO | 2015010084 A1 | 1/2015 | | |
| WO | WO-2015010084 A1 * | 1/2015 | ......... | A61K 31/6615 |

OTHER PUBLICATIONS

Evans et al. "Measurement of Gastrointestinal PH Profiles in Normal Ambulant Human Subjects." Gut, vol. 29, No. 8, Aug. 1988, pp. 1035-1041., doi:10.1136/gut.29.8.1035. (Year: 1988).*

(Continued)

*Primary Examiner* — Jennifer Wecker
*Assistant Examiner* — Michael Paul Shimek
(74) *Attorney, Agent, or Firm* — Barnes & Thornburg, LLP

(57) ABSTRACT

A process for quantifying the amount of unbound metal and bound metal in solution is provided. A process for quantifying the amount of bound metal amino acid chelate and free ligand in a solid (e.g., dry mixture such as an animal feed) is also provided.

6 Claims, 14 Drawing Sheets

(56) References Cited

OTHER PUBLICATIONS

Allen, Lindsay H. Advantages and Limitations of Iron Amino Acid Chelates as Iron Fortificants. Nutrition Reviews, vol. 60, No. suppl . 7, 2002, doi:10.1301/002966402320285047. (Year: 2002).*

De Carli et al. "Equilibrium, Thermoanalytical and Spectroscopic Studies to Characterize Phytic Acid Complexes with Mn(II) and Co(II)." Journal of the Brazilian Chemical Society, vol. 20, No. 8, 2009, pp. 1515-1522., doi:10.1590/s0103-50532009000800019. (Year: 2009).*

EFSA FEEDAP Panel. "Safety and Efficacy of Iron Compounds (EI) as Feed Additives for All Animal Species: Ferrous Carbonate; Ferric Chloride, Hexahydrate . . . " EFSA Journal, vol. 14, No. 2, 2016, doi:10.2903/j.efsa.2016.4396. (Year: 2016).*

Allen, Lindsay H. "Advantages and Limitations of Iron Amino Acid Chelates as Iron Fortificants" Nutrition Reviews, vol. 60, No. suppl. 7, 2002.

Cornforth. "Potential Use of Phytate as an Antioxidant in Cooked Meats." Food Phytates, by N. R. Reddy and Shridhar K. Sathe, CRC Press, 2002, pp. 199-200.

De Carli et al. "Equilibrium, Thermoanalytical and Spectroscopic Studies to Characterize Phytic Acid Complexes with Mn(II) and Co(II)." Journal of the Brazilian Chemical Society, vol. 20, No. 8, 2009, pp. 1515-1522.

Evans et al. "Measurement of Gastrointestinal PH Profiles in Normal Ambulant Human Subjects." Gut, vol. 29, No. 8, Aug. 1988, pp. 1035-1041.

EFSA FEEDAP Panel. "Safety and Efficacy of Iron Compounds (E 1) as Feed Additives for Alf Animal Species: Ferrous Carbonate; Ferric Chloride, Hexahydrate; Ferrous Fumarate; Ferrous Sulphate. Heptahydrate; Ferrous Sulphate, Monohydrate; Ferrous Chelate of Amino Acids, Hydrate; Ferrous Chelate of Glycine, Hydrate, Based on a Dossier Submitted by FEFANA Asbl." EFSA Journal. vol. 14, No. 2, 2016.

International Search Report for PCT/US2019/031679, dated Jul. 26, 2019.

* cited by examiner

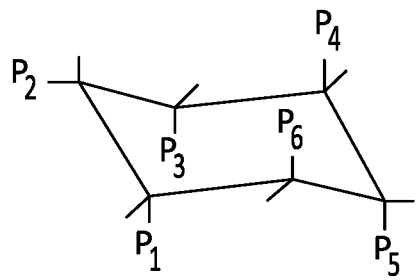
STRUCTURE I
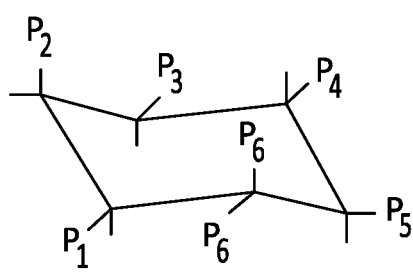
STRUTURE II
FIG. 1
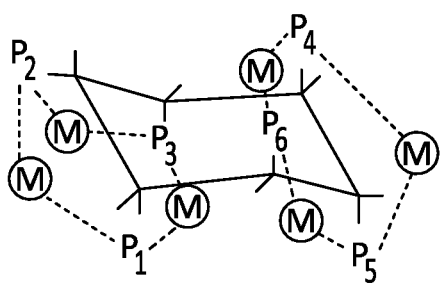
STRUCTURE IIIa
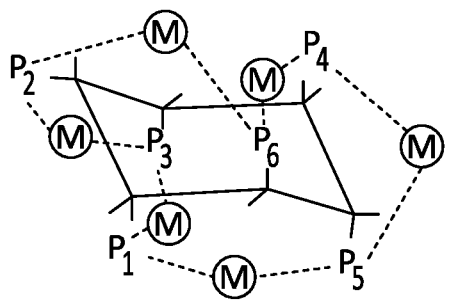
STRUCTURE IIIb
FIG. 2

| Sample | % Cu Chelate | %Glycine | Addition %Rutile |
|---|---|---|---|
| Y 18-119 | 0 | 0 | 100 |
| F 18-146 | 100 | 0 | 0 |
| J 18-78 | 0 | 100 | 10 |
| Y 18-226 | 20 | 80 | 10 |
| Y 18-225 | 40 | 60 | 10 |
| Y 18-224 | 50 | 50 | 10 |
| Y 18-223 | 60 | 40 | 10 |
| Y 18-227 | 80 | 20 | 10 |
| Y 18-222 | 100 | 0 | 10 |

| Sample | % Zn Chelate | %Glycine | Addition %Rutile |
|---|---|---|---|
| Y 18-119 | 0 | 0 | 100 |
| Y 18-216 | 100 | 0 | 0 |
| Y 18-221 | 80 | 20 | 10 |
| Y 18-217 | 60 | 40 | 10 |
| Y 18-218 | 50 | 50 | 10 |
| Y 18-219 | 40 | 60 | 10 |
| Y 18-220 | 20 | 80 | 10 |

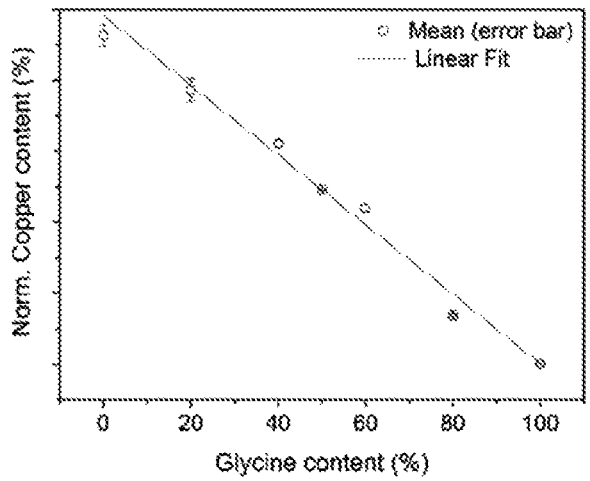
| Equation | y= a + b*x | | |
|---|---|---|---|
| Weight | Instrumental | | |
| Residual Sum of Squares | 338.50338 | | |
| Pearson's r | -0.99974 | | |
| Adj. R-Square | 0.99938 | Value | Standard Error |
| I1 | Intercept | 98180.47136 | 997.18219 |
| | Slope | -980.78751 | 9.97454 |
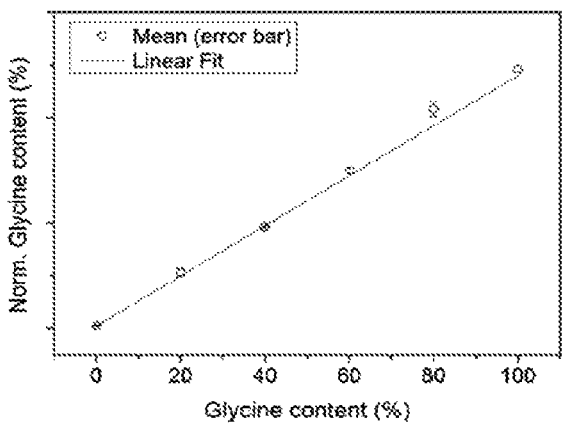
| Equation | y= a + b*x | | |
|---|---|---|---|
| Weight | Instrumental | | |
| Residual Sum of Squares | 16.91878 | | |
| Pearson's r | 0.99966 | | |
| Adj. R-Square | 0.99914 | Value | Standard Error |
| H1 | Intercept | 240.9897 | 86.88303 |
| | Slope | 237.41664 | 3.11676 |
FIG. 12

|   | N ANALYSES | N MISSING | MEAN | Estándar desviation | SE Of Mean |
|---|---|---|---|---|---|
| A | 3 | 0 | 8665.3 | 79.4 | 45.84 |
| B | 3 | 0 | 92055.33 | 438.26 | 253.03 |
| C | 3 | 0 | 9952.33 | 158.24 | 91.36 |
| D | 3 | 1 | 10266.33 | 299.01 | 172.63 |
| E | 3 | 0 | 10822.66 | 131.02 | 75.64 |
| F | 3 | 0 | 113797.66 | 403.035 | 232.69 |
| G | 3 | 0 | 11721.6666 | 188.47 | 108.81 |

Overall ANOVA

|   | DF | Sum Of Squares | MEAN SQUARE | F VALUE | PROB>F |
|---|---|---|---|---|---|
| Model | 8 | 2.24 E7 | 3.75E+06 | 49.66 | 1.21 E8 |
| Error | 14 | 1.06E+06 | 75422.47 |   |   |
| Total | 20 | 2.35E+07 |   |   |   |

| R-SQUARES | Coeff Var | Root MSE | Data Mean |
|---|---|---|---|
| 0.955512 | 0.02669 | 274.83163 | 10289.904 |

FIG. 13

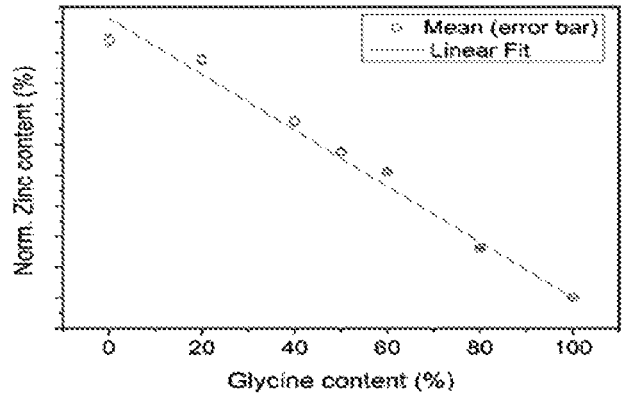
| Equation | y= a + b*x | | |
|---|---|---|---|
| Weight | Instrumental | | |
| Residual Sum of Squares | 432,78506 | | |
| Pearson's r | -0,9943 | | |
| Adj. R-Square | 0,98637 | Value | Standard Error |
| K1 | Intercept | 182593,57488 | 8747,95834 |
| | Slope | -1824,91845 | 87,48034 |
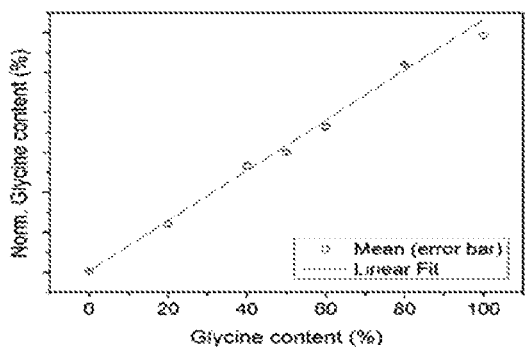
| Equation | y= a + b*x | | |
|---|---|---|---|
| Weight | Instrumental | | |
| Residual Sum of Squares | 457,66422 | | |
| Pearson's r | 0,99767 | | |
| Adj. R-Square | 0,99441 | Value | Standard Error |
| H1 | Intercept | 154,88945 | 55,79441 |
| | Slope | 314,29054 | 9,61956 |
FIG. 14

|   | N ANALYSES | N MISSING | MEAN | Estándar desviation | SE Of Mean |
|---|---|---|---|---|---|
| A | 3 | 23 | 7713.666667 | 284.81 | 164.4 |
| B | 3 | 0 | 8406.3 | 88.88 | 51.3 |
| C | 3 | 0 | 8924 | 360.27 | 208 |
| D | 3 | 0 | 9308 | 116.31 | 67.15 |
| E | 3 | 0 | 1014.3 | 232.79 | 134.4 |
| F | 3 | 0 | 10968.3 | 245.31 | 141.63 |
| G | 3 | 0 | 11721.6 | 188.47 | 108.91 |

Overall ANOVA

|   | DF | Sum Of Squares | MEAN SQUARE | F VALUE | PROB>F |
|---|---|---|---|---|---|
| Model | 8 | 3.66 E7 | 6100035 | 111.71 | 5.21E-11 |
| Error | 14 | 7764496 | 544606.85 |   |   |
| Total | 20 | 3.73666eE7 |   |   |   |

|   | R-SQUARES | Coeff Var | Root MSE | Data Mean |
|---|---|---|---|---|
|   | 0.97954 | 0.024434 | 233.6811 | 9598.8 |

FIG. 15

| Sample cooper chelate | Concentration STD Cu (ppm) | area A | area B | area C | area A+B+C | area Prom | %RSD | %VC |
|---|---|---|---|---|---|---|---|---|
| STD Cu 100 | 100 | 148511 | 405 | 15190 | 164106 | 162967,333 | 4030,49443 | 2,47319162 |
| STD Cu 100 | 100 | 150500 | 457 | 15349 | 166306 | | | |
| STD Cu 100 | 100 | 143372 | 336 | 14782 | 158490 | | | |
| STD Cu 200 | 200 | 291617 | 1020 | 39533 | 332170 | 335459 | 4985,32978 | 1,48612193 |
| STD Cu 200 | 200 | 299849 | 1057 | 40289 | 341195 | | | |
| STD Cu 200 | 200 | 292832 | 1040 | 39140 | 333012 | | | |
| STD Cu 500 | 500 | 808472 | 4092 | 139794 | 952358 | 975612 | 20317,9483 | 2,08258491 |
| STD Cu 500 | 500 | 845257 | 3806 | 140870 | 989933 | | | |
| STD Cu 500 | 500 | 840642 | 3838 | 140065 | 984545 | | | |
| STD Cu 700 | 700 | 1234133 | 5219 | 205147 | 1444499 | 1459800,33 | 17079,8208 | 1,17001075 |
| STD Cu 700 | 700 | 1249461 | 5006 | 202208 | 1456675 | | | |
| STD Cu 700 | 700 | 1265069 | 5009 | 208149 | 1478227 | | | |
| STD Cu 1000 | 1000 | 1725602 | 6827 | 285634 | 2018063 | 2032073,33 | 12209,7887 | 0,60085374 |
| STD Cu 1000 | 1000 | 1769386 | 5819 | 262509 | 2037714 | | | |
| STD Cu 1000 | 1000 | 1766383 | 5862 | 268198 | 2040443 | | | |

FIG. 16

| Sample | area A | area B | area C | area A+B+C | concentration exp (ppm) Curve | Concentration theoretical (ppm) | % accuracy |
|---|---|---|---|---|---|---|---|
| STD Cu 100 | 148511 | 405 | 15190 | 164106 | 105,86 | 100,2 | 105,65 |
| STD Cu 100 | 150500 | 457 | 15349 | 166306 | 106,92 | 100,2 | 106,71 |
| STD Cu 100 | 143372 | 336 | 14782 | 158490 | 103,14 | 100,2 | 102,94 |
| STD Cu 200 | 291617 | 1020 | 39533 | 332170 | 187,14 | 200,4 | 93,38 |
| STD Cu 200 | 299849 | 1057 | 40289 | 341195 | 191,50 | 200,4 | 95,56 |
| STD Cu 200 | 292832 | 1040 | 39140 | 333012 | 187,54 | 200,4 | 93,58 |
| STD Cu 500 | 808472 | 4092 | 139794 | 952358 | 487,06 | 501 | 97,22 |
| STD Cu 500 | 845257 | 3806 | 140870 | 989933 | 505,23 | 501 | 100,85 |
| STD Cu 500 | 840642 | 3838 | 140065 | 984545 | 502,63 | 501 | 100,33 |
| STD Cu 700 | 1234133 | 5219 | 205147 | 1444499 | 725,06 | 701,4 | 103,37 |
| STD Cu 700 | 1249461 | 5006 | 202208 | 1456675 | 730,95 | 701,4 | 104,21 |
| STD Cu 700 | 1265069 | 5009 | 208149 | 1478227 | 741,38 | 701,4 | 105,70 |
| STD Cu 1000 | 1725602 | 6827 | 285634 | 2018063 | 1002,44 | 1002 | 100,04 |
| STD Cu 1000 | 1769386 | 5819 | 262509 | 2037714 | 1011,95 | 1002 | 100,99 |
| STD Cu 1000 | 1766383 | 5862 | 268198 | 2040443 | 1013,27 | 1002 | 101,12 |
| | | | | | | Valor Max | 106,71 |
| | | | | | | Valor Min | 93,38 |

FIG. 17

| Concentration Cu (ppm) | Sum of areas | | |
|---|---|---|---|
| | Curve 1 | Curve 2 | Curve 3 |
| 100,00 | 164106 | 180004 | 175211 |
| | 166306 | 157898 | 175418 |
| | 158490 | 165772 | 169032 |
| 200,00 | 330104 | 356667 | 362543 |
| | 352195 | 334523 | 347957 |
| | 333012 | 371292 | 368638 |
| 500,00 | 952358 | 927912 | 1007579 |
| | 989933 | 953632 | 969696 |
| | 984545 | 1013644 | 960086 |
| 700,00 | 1444599 | 1439245 | 1361618 |
| | 1456675 | 1374731 | 1446590 |
| | 1357827 | 1357861 | 1427746 |
| 1000,00 | 2018063 | 1933023 | 1933621 |
| | 1937714 | 1988746 | 1974646 |
| | 2040443 | 2081456 | 2107736 |

| Summary | Counts | Sum | Mean | Variance |
|---|---|---|---|---|
| Row 1 | 3 | 519321 | 173107 | 66506713 |
| Row 2 | 3 | 499622 | 166540,6667 | 76778901,3 |
| Row 3 | 3 | 493294 | 164431,3333 | 29131481,3 |
| Row 4 | 3 | 1049314 | 349771,3333 | 298734844 |
| Row 5 | 3 | 1034675 | 344891,6667 | 85122097,3 |
| Row 6 | 3 | 1072942 | 357647,3333 | 456935665 |
| Row 7 | 3 | 2887849 | 962616,3333 | 1665632774 |
| Row 8 | 3 | 2913261 | 971087 | 330891811 |
| Row 9 | 3 | 2958275 | 986091,6667 | 718908974 |
| Row 10 | 3 | 4245462 | 1415154 | 2156743801 |
| Row 11 | 3 | 4277996 | 1425998,667 | 1996707040 |
| Row 12 | 3 | 4143434 | 1381144,667 | 1628763490 |
| Row 13 | 3 | 5884707 | 1961569 | 2393768428 |
| Row 14 | 3 | 5901106 | 1967035,333 | 694507941 |
| Row 15 | 3 | 6229635 | 2076545 | 1150175403 |
| Column 1 | 15 | 14686370 | 979091,3333 | 4,9598E+11 |
| Column 2 | 15 | 14636406 | 975760,4 | 4,8624E+11 |
| Column 3 | 15 | 14788117 | 985874,4667 | 4,8873E+11 |

FIG. 18

| ANALYSIS OF VARIANCE | | | | | | |
|---|---|---|---|---|---|---|
| Origin of variations | Sum of squares | Degrees of freedom | Average of squares | F | Probability | Critical value of F |
| Columns | 797001796 | 2 | 398500898,1 | 0,41787826 | 0,662481176 | 3,34038556 |
| Error | 2,6702E+10 | 28 | 953629176,3 | | | |
| Total | 2,0594E+13 | 44 | | | | |

FIG. 18 Continued

PROCESS FOR QUANTIFICATION OF METAL AMINO ACID CHELATES IN SOLUTIONS AND SOLIDS

CROSS-REFERENCE TO RELATED APPLICATIONS

The present application claims priority to U.S. provisional application Ser. No. 62/670,202, filed May 11, 2018, the contents of which are incorporated herein in its entirety.

BACKGROUND

Metal amino acid chelates and other essential metal/mineral organic sources offer benefits and greater differential bioavailability compared to inorganic sources in animal and human nutrition. The reaction of metals and amino acids to form chelate molecules is a complex reaction. Frequently, manufacturers or commercial synthesizers of these molecules, due to incomplete understanding of chelation chemistry, do not fully apply any analysis to their synthesis processes which results in a complex set of non-stable commercial organic type molecules that are categorized as chelates. The requirement of the heterocyclic ring structure is not reached, and, instead, a series of complexes are obtained due to uncontrolled reaction between the amino acid and the metal salts or minerals. The result is the formation of other types of complexes that may differ in their chemical structure and therefore in their bioavailability or diffusion through the small intestine. As result of the dose given, the effectiveness may vary according with the synthesis products obtained in different batches in the absence of complete characterization of the synthesis products. (Ashmead, 2012).

There exists a need for methodologies for the synthesis of metal amino acid chelates and the establishment of analytical controls that allow monitoring, characterization, evaluation of comparative stability and continuous improvement of the synthesis process to achieve the chemical structure desired to ensure an effective, high concentration dose of bound metal/mineral to an animal. To ensure an effective, high concentration of bound metal/mineral, the amino acid chelate must exhibit less reactivity with other antagonistic metal/mineral sources of the diet. Due to the unpredictability and lack of stability of amino acid chelates, production costs remain high. The ability to quantify and asses the stability of amino acid chelates will decrease the cost of formulations by the inclusion of them in a lower quantity and allow for greater performance of the animal. Additionally, antagonistic reactions may be avoided allowing for greater solubility of these compounds at the different physiological conditions (e.g., pH) and avoiding putting at risk the stability of the premixes due to the inclusion of a highly reactive species from an unbound metal/mineral source. The has been an exhaustive search for a lower interaction and reactivity of sources of calcium, zinc, and copper with other chelating and/or sequestering sources such as phytic acid present in the cereals of the animal's diet. The metal amino acid chelates are be good alternatives of greater bioavailability, solubility and less reactivity due to the fact that they act as coordination compounds. Thus, the amino acid chelates can be evaluated against a competitor (i.e., exerted by phytic acid) and the structural stability assessed in solution under simulated physiological conditions media.

Phytic acid has the ability to form complexes with essential trace metals or mineral (Cu, Cr, Zn, Co, Mn, Fe, and Ca), which decreases their intestinal absorption and bioavailability in monogastric animals because such animals are not provided with sufficient endogenous phosphatases that are capable of releasing the metals/minerals from the phytate structure. In addition, phytates interact with basic protein residues forming complexes, such as protein-phytate and phyto-metal/mineral protein. (NADA M. TAMIM AND ROSELINA ANGEL 2003).

The reaction between phytic acid and an essential trace metal or mineral favors the formation of highly stable complexes that precipitate in basic media (e.g., at intestinal pH). As consequence of precipitation, proteins transport located in the intestinal cells for the metallic metal cannot act because the metal is not in the ionic form or soluble form. The same principle is applicable to other substances commonly found in the diet such as oxalates and phosphates. In fact, calcium, magnesium, zinc, iron and aluminum, react with dietary phosphates to form insoluble precipitates. The basic environment of the intestine reduces the tendency of the solubility of these when entering into this environment. When the metal/mineral is trapped in a compound of insoluble type, there is a small probability of a significant absorption of the precipitated salt. Thus, there exists a need for analytical testing methods that validate and quantify bound and unbound metal or mineral content under in vitro conditions.

BRIEF DESCRIPTION OF THE FIGURES

FIG. 1 provides a schematic structure of phytic acid in the axial form (Structure I) and in the equatorial form (Structure II). The letters P 1, P2, . . . , P6 represent phosphate groups.

FIG. 2 illustrates possible coordinate bonding of metal cations to pairs of oxo di-anions of phytic acid in the axial conformation. Bonding sites are those that can be constructed from CPK space-filling models.

FIG. 12 provides calibration curves for copper amino acid chelate samples.

FIG. 13 provides statistical data ANOVA for rutile compound acting as witness in the calibration matrix for copper compounds.

FIG. 14 provides calibration curves for zinc amino acid chelate samples.

FIG. 15 provides statistical data ANOVA for rutile compound acting as witness in the calibration matrix for zinc compounds.

FIG. 16 is a table that shows Repeatability data for the evaluation of copper bisglycinate HPLC-DAD methodology.

FIG. 17 is a table that shows the accuracy evaluated by triplicate at 253 nm by cooper bisglycinate at 5 different concentrations is between 93 and 106%.

FIG. 18 provides a Statistical analysis ANOVA developed to different levels of calibration at 253 nm. Experimental F is lower than F Critical.

SUMMARY OF THE DISCLOSURE

Figure 3:
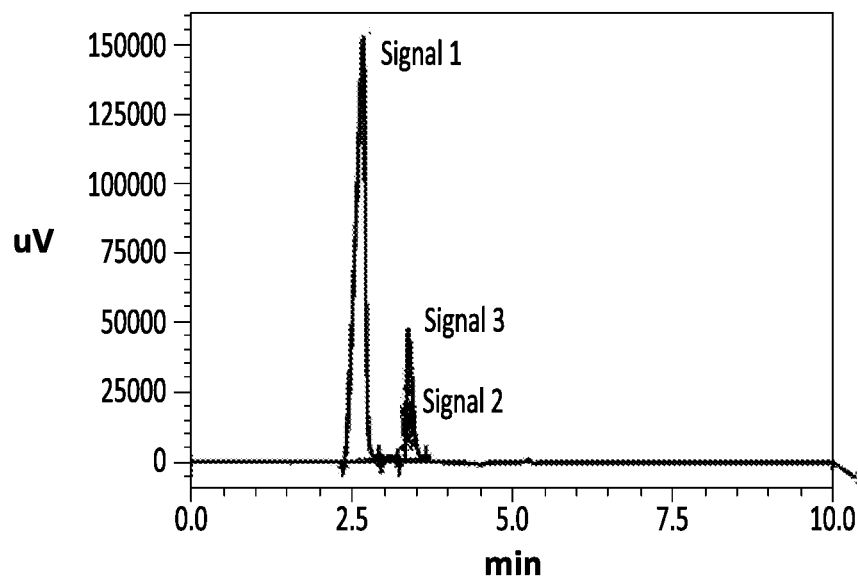
FIG. 3 is a HPLC chromatogram to 253 nm with peaks 1, 2, 3 cooper chelate.

According to one aspect, a process for quantifying the amount of unbound metal and bound metal in solution is provided. The method includes the step of:

(a) reacting a metal compound with phytic acid in an aqueous solution;

(b) adjusting the pH of the aqueous solution to about 5.0 to about 7.0;

(c) analyzing an aliquot of the solution from step (b) via high performance liquid chromatography to determine the amount of free ligand and amount of bound metal; and (d) analyzing total metal content via an inductively coupled plasma (ICP) technique to determine the total amount of metal present in solution and the amount of any insoluble metal precipitate produced after step (b). According to one embodiment, prior to step (b), the aqueous solution has an initial pH corresponding to the physiological pH of the stomach, gizzard or small intestine. According to one embodiment, prior to step (b), the aqueous solution has an initial pH of about 3.0. According to one embodiment, the bound metal is in the form of a metal amino acid chelate. According to one embodiment, the metal is selected from the group consisting of Cu, Cr, Zn, Co, Mn, Fe, and Ca. According to one embodiment, the pH of the solution in step (b) is adjusted to a pH of about 6.0.

According to one aspect, a process for quantifying the amount of bound metal amino acid chelate and free ligand in a solid is provided. The includes the steps of:

(a) qualitatively analyzing a solid sample via x-ray crystallography to obtain an x-ray pattern;

(b) comparing the X-ray pattern of the solid sample from step (a) with one or more x-ray patterns from a reference database; and (c) determining the amount of bound metal amino acid chelate and free ligand in the solid based on the solid x-ray diffraction intensity. According to one embodiment, the step of comparing the X-ray pattern of the solid sample with x-ray patterns from a reference database, can be followed by a structural refinement process via the Rietveld method. According to one embodiment, the solid is an animal feedstock.

DETAILED DESCRIPTION OF THE DISCLOSURE

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The term "chelate" as used herein means a molecular entity made up of a central metal associated with at least one bidentate ligand and optionally associated with one or more mono- or multi-dentate ligands. In the interaction between the central metal and any of the ligands, the bonds between the ligand and the central metal can include covalent bonds, ionic bonds, and/or coordinate covalent bonds.

The term "ligand" as used herein means a molecular group that is associated with a central metal atom. The ligand can be any ligand capable of forming a chelate with a metal. The ligand is preferably easily metabolized by an animal.

The term "metal amino acid chelate" as used herein means the product resulting from the reaction of a metal or metal ion from a soluble metal salt with one or more amino acids. Particularly, a metal amino acid chelate includes the product resulting from the reaction of a metal ion with amino acids having a mole ratio of one mole metal to one to three moles of amino acids to form coordinate covalent bonds. The resulting molecule may include two or three five-member heterocyclic ring structures containing a metal ion. The metal ion is attached by coordinate covalent bonds to two or more nonmetals in the same molecule. The term also refers to a particular class of mineral or mineral compound. The metal amino acid chelate is nutritionally function. Metal amino acid chelates provide superior bioavailability and lower toxicity compared to other mineral or mineral compounds. According to one embodiment, the metal amino acid chelates as provided herein have a molecular weight of less than or equal to 800 daltons (AMU).

The term "metal" refers to any alkaline, alkaline earth, transition, and rare earth, basic, and semi-metals which can coordinate with a ligand and can also be used interchangeably with the term "mineral" which refers to a metal compound and includes any trace mineral beneficial to an animal diet (e.g., Copper, Zinc, Cobalt, Manganese, Iron, and Calcium).

The term "phytic acid" used herein refers to the phosphate compound found in many plant tissues that is less digested by monogastric animal and by humans. Phytic acid interacts with metal amino acid chelates and may decrease the absorption of trace metal nutrient bioavailability.

A process for quantifying the metal amino acid chelates in solutions and in solids is provided. According to a particular embodiment, the process provides for the analysis of chelates and quantifies the bounded metal in solution as well as the stability constant relative to the competitor, phytic acid, which is frequently found in animal feeds. A process for quantifying the stability of all metal amino acid chelates is provided including quantifying the percentage of chelation in solution and in solids (e.g., dry mixture).

The processes as provided herein may be utilized to evaluate commercial chelates and to compare the stability and quality of such commercial chelates. The processes as provided herein also allows for the monitoring of the speed of comparative dilution by modifying the size of the crystal in vitro to increase solubility and bioavailability. The processes as provided herein allow for the monitoring and quantification of the effectiveness of the synthesis (commercial production) of metal amino acid chelates as solids. The processes as provided herein may also be utilized for quality control purposes during production of animal feed. The processes as provided herein utilize HPLC which allows confirmation of the stability of a cluster of chelates observed in previous x-rays and confirms the presence of chelates that remain in solution. The HPLC and X-ray diffraction analysis also allows the determining of the crystalline structure information, and therefore, allows an assessment of which crystalline structure prevails in solution thereby providing an insight as to how to synthesize more bioavailable compounds.

FIGS. 1 and 2 depicts schematic structures of phytic acid in the axial form (Structure 1) and in the equatorial form (Structure II). The letters P 1, P2, . . . , P6 represent the phosphate groups which can react with metal and they can ionized in different order depend on pH. At normal pH range, the phosphate groups of phytic acid are negatively charged, allowing interaction with positively charged components such as metals/minerals and proteins. Metal ions may bind with one or more phosphate groups forming complexes of varying solubility. Proteins are able to bind directly with phytic acid through electrostatic charges. Zinc appears to be the most affected by phytic acid because it forms the most stable and insoluble complex. Other metals/minerals and nutrients that are affected include calcium (Ca), sodium (Na), iron (Fe), magnesium (Mg), manganese (Mn), and chlorine (Cl) and others such as Cu,(cooper) and Cr, (chromium)

FIG. 2 shows how metal ion can be kidnapped by phytic acid as consequence of pH media. Phosphates group are completely ionized at basic pH and can form macromolecular complex with metal. Research has traditionally focused on phytic acid's unique structure that provides the ability to bind metals/minerals, proteins, and starch, and the resulting detrimental effects. Phytic acid has also been attributed to high phosphorus excretion by monogastric animals and the resulting environmental problems of phosphorus pollution of water and soil.

FIG. 3 depicts cooper chelate chromatogram on it there are three different picks all of them belong to chelate, because in solution cooper chelate can form clusters mono, di, tri gicynates could be present and can form aggregates.

Figure 4:
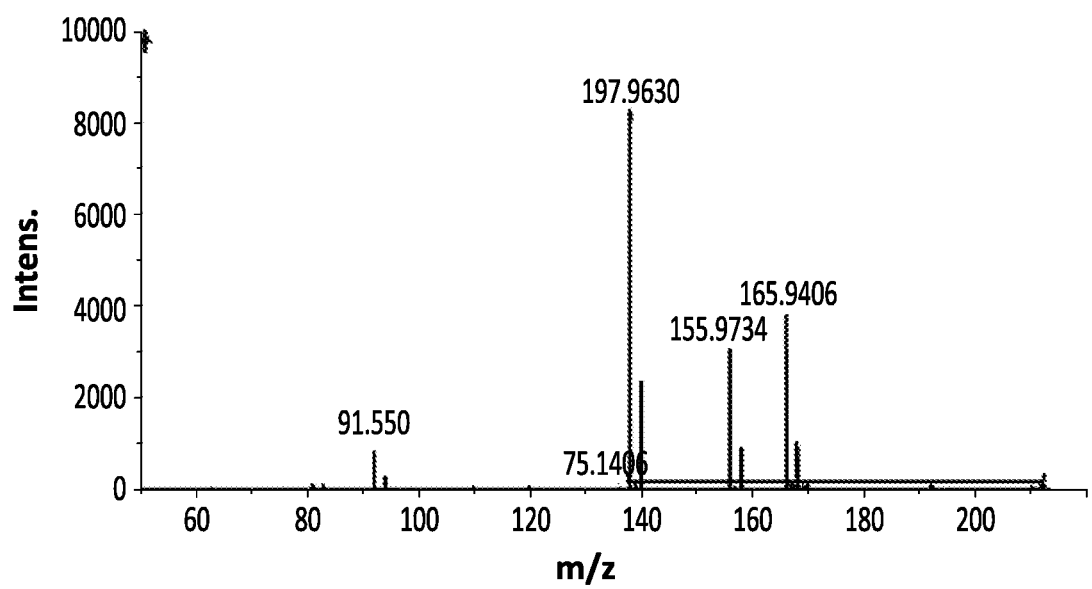
FIG. 4 is cooper bisglycinate Masses fragment by UHPLC tandem masses.
Figure 5:
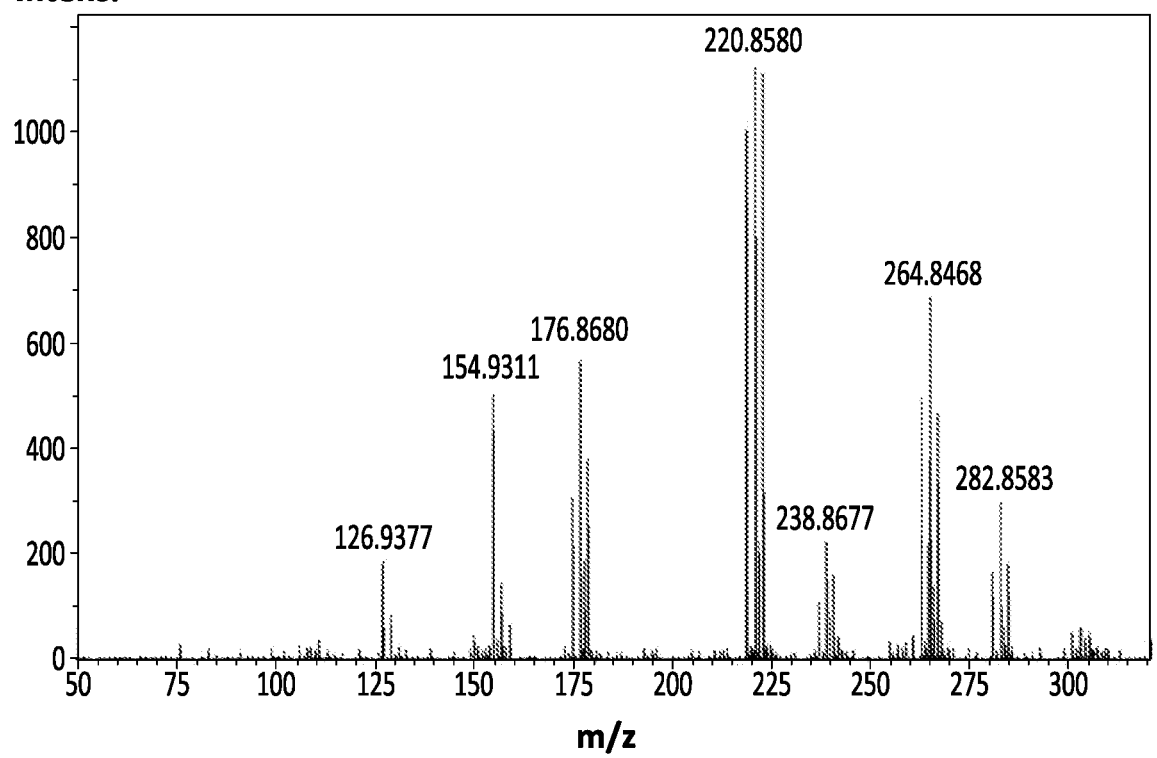
FIG. 5 Fragments UHPLC masses/masses zinc triglicinate with a possible one molecule of water bound and subsequent losses of 44 m/z FIG. 6 Linearity copper chelate validation developed by HPLC-DAD 253 nm FIG. 7 XRD pattern of copper amino acid Chelate sample obtained as single-phase.

FIG. 4 depicts HPLC masses fragments of cooper bisglycinate, the fragment pattern is to molecular pick ion of 211.98 $M^+$ FIG. 5 depicts the molecular ion pick 305.8743 (cation formed by the initial molecule of the analyzed substance less one electron) corresponding to zinc triglicinate with a possible one molecule of bound water. Subsequent losses of 44 m/z are present due to a loss of fragments characterized by a carboxyl group.

Figure 6:
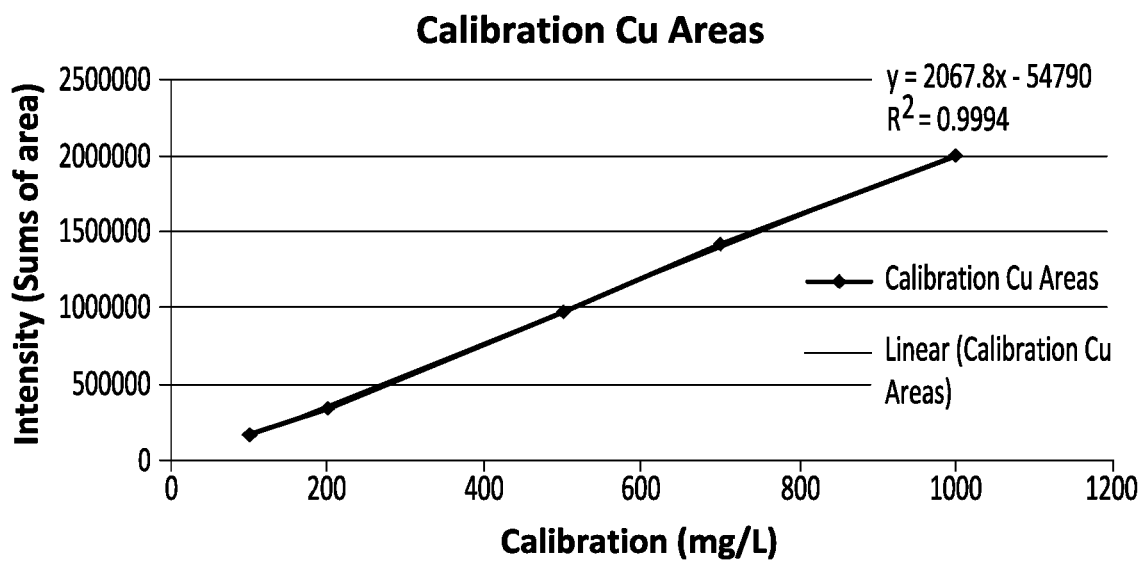

FIG. 6 depicts the calibration curve validation of cooper bisglycinate obtained by high performance chromatography. A diodes arranged detector obtained linearity of $r^2$ 0.9994 (coefficient correlation). The calibration was successfully and illustrated the analytic methodology was lineal.

Figure 7:
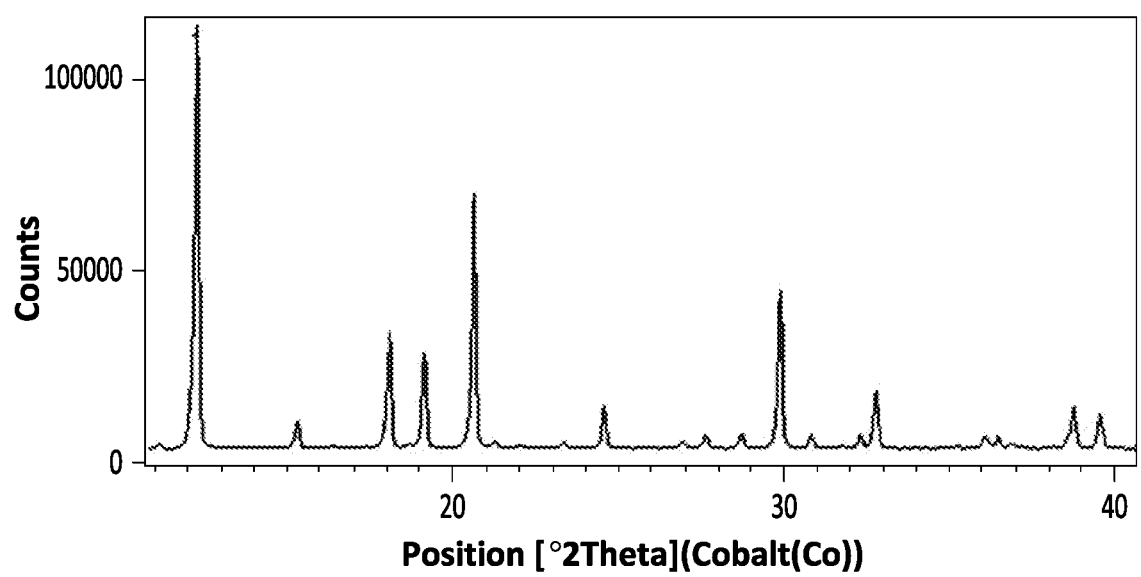
Figure 8:
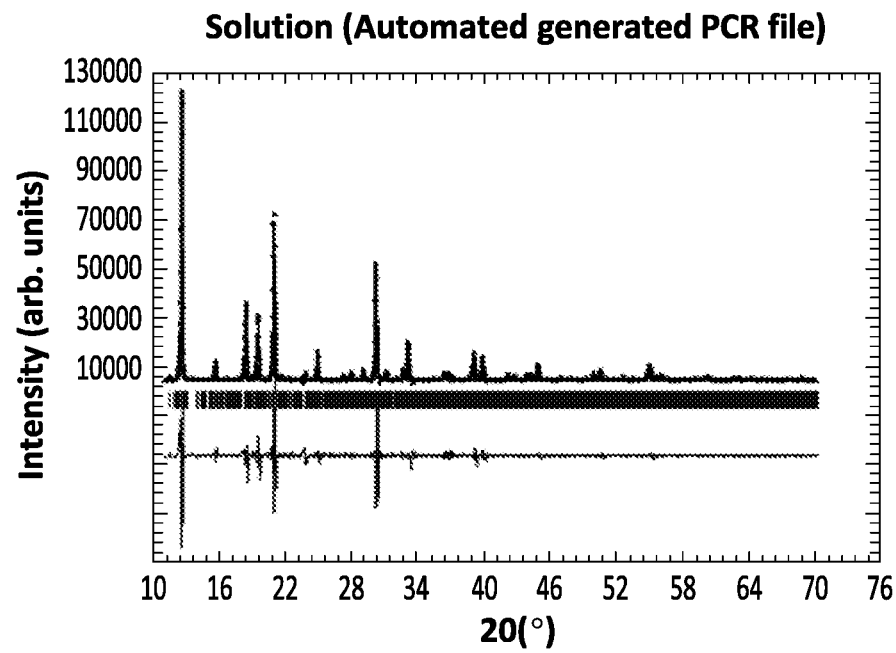
FIG. 8 provides an example of Rietveld refinement for copper amino acid chelate sample.

FIGS. 7 and 8 depicts cooper bisglycinate diffractogram by XRD (Ray X diffraction). FIG. 8 depicts the riveted refinement developed based on crystallographic information from scientific literature and the experimental cooper bisglycinate diffractogram. The final refinement was made using the Fullprof software (available from Fullprof suite).

Figure 9:
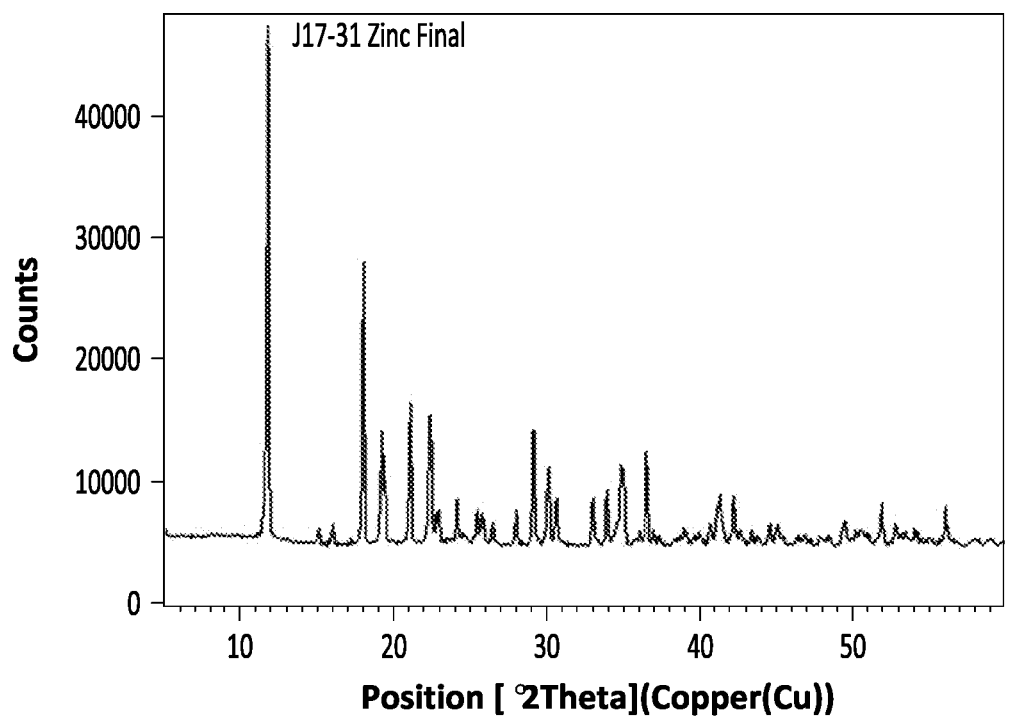
FIG. 9 provides an XRD pattern of zinc amino acid chelate sample obtained as single-phase.

FIG. 9 depicts a zinc bisglycinate diffractogram bases on the riveted refinement.

Figure 10:
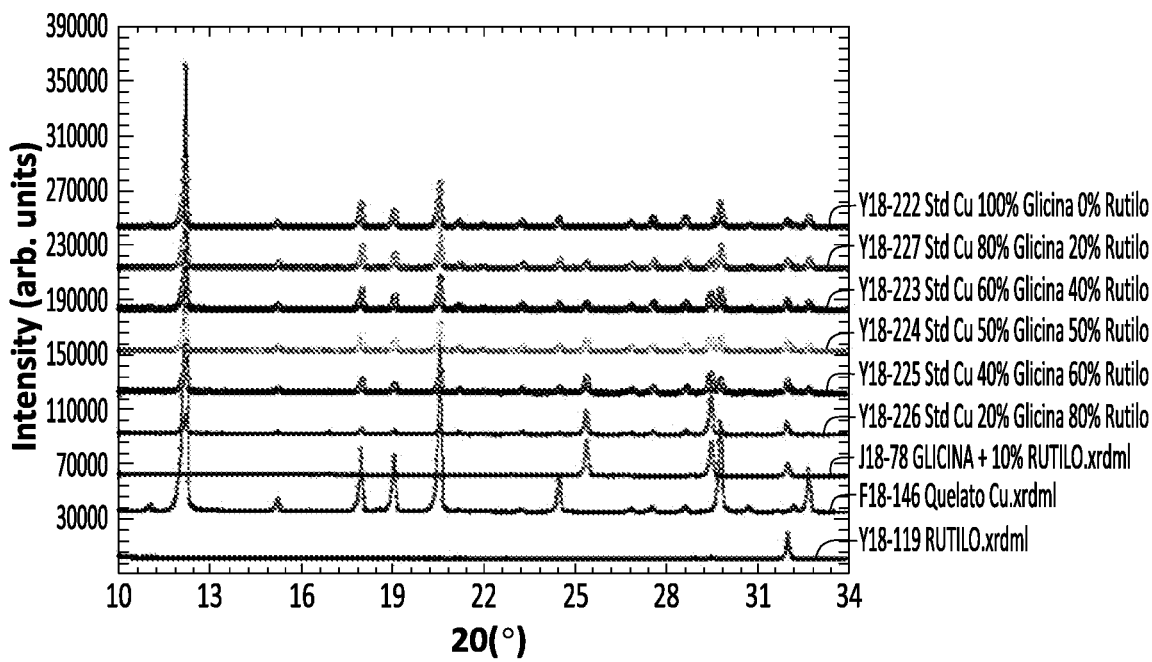
FIG. 10 provides calibration XRD patterns for copper amino acid chelate samples.
Figure 11:
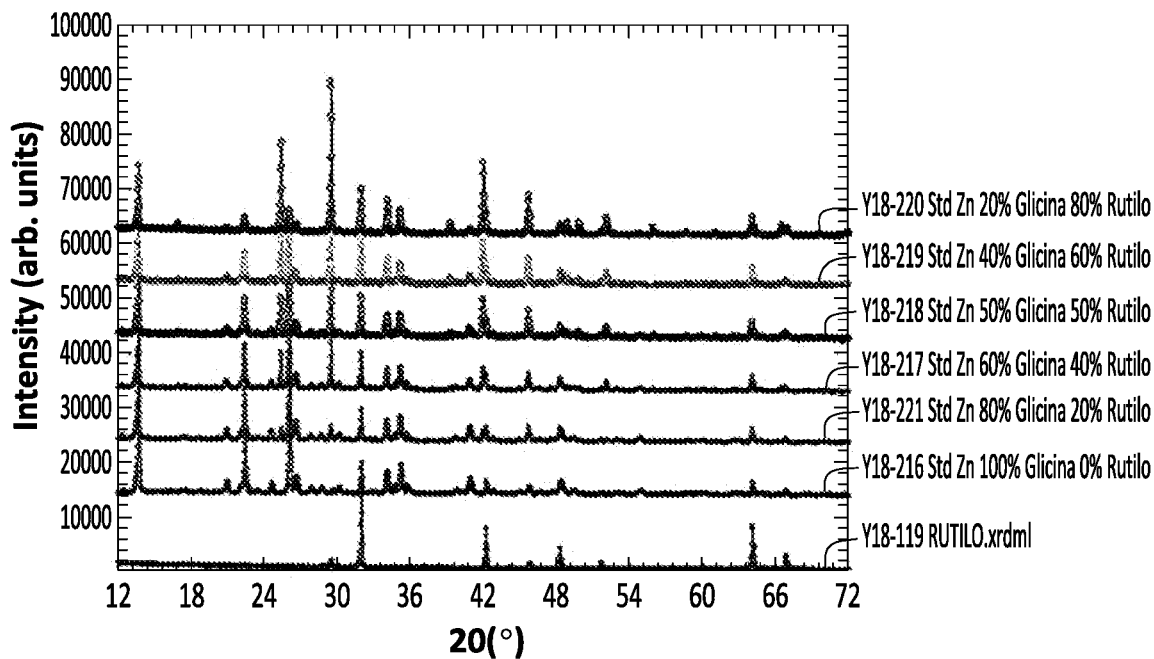
FIG. 11 provides calibration XRD patterns for zinc amino acid chelate samples.

FIGS. 10 and 11 depict a calibration by XRD of cooper bisglycinate and zinc bisglycinate. Calibration was built using different samples spiked with the free ligand, glycine. Rutile was used as internal standard.

FIGS. 12 and 13 depict parameters of validation of the methodology developed by XRD. Linearity of method was adequate to cooper and zinc bisglycinate. Method repeatability was developed by ANOVA analyses.

According to one embodiment, the process for quantifying the metal amino acid chelates in solids includes the step of performing X-ray diffraction on a solid. According to a particular embodiment, powder x-ray diffraction analysis is performed. According to one embodiment, the step of performing x-ray diffraction includes the application of electromagnetic X-ray wave radiation interacting with matter that is partially scattered and finally diffracted until fulfillment of the Bragg equation. Such methodology may not depend on single-crystal or/and single-phase samples to get high quality and accurate results and may, instead, provide a preliminary phase identification via cluster analysis based on crystallographic reference databases. Such databases are publicly available. According to a particular embodiment, a crystal structure determination (e.g., CIF) provides a means to determine the content of a crystalline phase by full pattern methods based on the Rietveld method. According to one embodiment, Rietveld refinement is a Whole Pattern Fitting Structure Refinement method for structural analysis of nearly all classes of crystalline materials not available as single crystals Such a software approach refines various metrics including lattice parameters, peak width and shape, and preferred orientation to derive a calculated diffraction pattern. Once the derived pattern is nearly identical to an unknown sample data, various properties pertaining to that sample can be obtained including, but not limited to, accurate quantitative information, crystallite size, and site occupancy factors. The process of refining the pattern is computationally intensive, requiring several minutes to calculate results for a multi-component mixture. According to one embodiment, several polymorphisms may be determined depending on the way of how the solids are prepared or based on the chemical nature of the organic metals/minerals themselves.

According to a particular embodiment, the qualitative identification of phases may be achieved by comparing the X-ray pattern of the solid sample containing metal amino acid chelates with patterns of a reference database (e.g., COD (Crystallography Open Database), ICDD (the international Centre for diffraction data) ICSD (Crystal structure database)). After qualitative analysis, semi quantitative phase analysis may be performed. To get reliable results, integral intensities of the reflections may be utilized with a limit of detection at a relative error of typically about 1%. According to one embodiment, a standard may be utilized and a background subtraction from at least a cubic polynomial as a baseline may be done. The standard may be titanium oxide, specifically rutile polymorph (95%) from Sigma-Aldrich (99% purity). Mainly reflections of rutile phase do not affect the quantitative determination of the organic metals/minerals analyzed. The reference intensity ratio (RIR) may be employed as a semi-quantitative analysis method as long as RIR values of the structure data is available.

According to one embodiment, the selected routine method includes a multi-phase identification, with constituents available as pure phases and a witness material added because a minimum overlap and similar absorption may be achieved. From a solid mixture, a calibration curve may be obtained under identical X-ray diffraction set-up conditions. With this absolute calibration method, a determination of the content of the solid chelate sample can be related to the direct measurement of intensities. These methods by addition of a known amount of the same phase of interest may be controlled by a rutile standard since some evidences of adducts between the metal chelate and the amino acid may be found from a solid state and solution reaction. According to one embodiment, crystallographic information data may be obtained via the Rietveld method.

According to one embodiment, the process of for quantifying the metal amino acid chelates in liquid is provided. According to one embodiment, the process includes the step of reacting a sample a liquid sample with phytic acid in an metal such as, for example, Fe, Mn, Cu, Zn, Fe, Co, Cr, or Ca. According to one embodiment, the reaction between the metals and the phytic acid may be carried out at a pH of typically from about 2.0 to about 7.5. According to a particular embodiment, the reaction between the metals and the phytic acid may be carried out at a pH of typically about 3.0.

According to one embodiment, at least one solution of sodium phytate may be add to one solution of metal/mineral to ensure phytate a ratio of about 6:1 of sodium phytate to metal/mineral or excess of phytate. The complex may be completely solubilized at a pH of about 3.0 which simulates gastric conditions in monogastric animals and gizzard in poultry. According to one embodiment, the pH may then be raised to typically about 4.0 to about 7.0. According to a particular embodiment, the pH may then be raised to typically about 6.0. According to one embodiment, homonuclear complexes of the metal/mineral and phytic acid may be formed at this pH range. According to one embodiment, such homonuclear complexes are released by competition with the metal/mineral which is not stabilized by a covalent coordinate bond as a metal amino acid chelate. An abundant precipitate may then be formed according to one embodiment. According to one embodiment, at a pH of typically about 6.0 the source of metal/mineral is not stable and reacts with phytic acid.

According to one embodiment, an aliquot of typically about 5 mL of the remainder solution at a pH of about 6.0 may be passed through an anionic exchange resin. Any unreacted phytic acid may then be eluted with typically about 10 ml of water. According to one embodiment, the metal amino acid chelate may then be retained and later eluted with 0.6 M HCL and water. According to one embodiment, stable unreacted metal amino acid chelate may be retained onto the anionic column. Stable unreacted metal amino acid chelate may then be eluted by a 0.6M solution of HCL with about 6 washes of typically about 5 ml. The metal amino acid chelate solution may then be analyzed by high performance liquid chromatograph (HPLC) (diodes arrange or mass detector or masses detector or masses detector).

According to an alternative embodiment, a visual testing method may be carried out. According to such an embodiment, phytic acid is reacted with a metal/mineral source producing a precipitate. The precipitate is then filtered. Any unstable metal/mineral precipitate may then be quantified by an inductively coupled plasma (ICP) technique. According to one embodiment, the ICP technique is a multi-element analysis technique that will dissociate a sample into constituent atoms and ions and exciting them to a higher energy level. The atoms and ion to emit light at a characteristic wavelength, which can be analyzed via Inductively Coupled Plasma-Atomic Emission Spectroscopy (ICP-AES) or Inductively Coupled Plasma Mass Spectrometry (ICP-MS).

According to one embodiment, an eluted sample may be injected into a high performance liquid chromatography (HPLC) device. Peaks may then monitored for a metal amino acid chelate, metal amino acid chelate and free ligand. According to one embodiment, the HPLC column is a reverse phase column. According to one embodiment, the mobile phase may be any acceptable mobile phase for the analysis as provided herein including one or more of ethanol, methanol, acidic water, formic acid, and acetonitrile.

The metal/mineral bounded or stable organic metal/mineral complex and chelate may be quantified using the elute of the retained chelate in the column with mobile phase. Colorless complexes such as Mn, Mg, Zn may be evaluated by passing through an OASIS polymeric cartridge (available from Waters Corporation, Milford, Mass. USA) functionalized by solid-liquid extraction to remove the ligand. According to one embodiment, the column allows clusters to be separated due to different charges.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

Example 1—Solid Chelate Analysis

The X-ray diffraction (XRD) measurements were obtained using an Empyrean X'pert XRD diffractometer available from the PANalytical Company. This XRD utilized a unique wavelength of Cu K$\alpha$1 (1.44556 A) and a 3D-solid state detector with 256 channels under a Bragg-Brentano optical focusing geometry and a $\omega$-2$\theta$ configuration. The step was 0.013° and the source of radiation was excited at 40 mA and 40 kV. All samples were run under the same set-up and a Si standard sample were randomly measured to check the system resolution and intensity counting. The samples were prepared on polymer sample holders of 27 mm of diameter for reflection measurements. The solid surface was completely flat with respect to the XRD ray path to fit the focusing circle of the instrument. The XRD data were then collected. The identification of the crystalline phases was achieved by comparing the X-ray pattern of the solid chelate sample with patterns of a reference database. For Cu and Zn amino acid chelate samples performed as references as shown in FIG. 7, a structural refinement procedure was carried out in order to get the crystalline structural information. The input crystallographic information was obtained from scientific literature and the output file containing the final refinement parameters was obtained by using the Fullprof software (available from Fullprof Suite).

After the qualitative analysis was performed, a set of samples were prepared for a semi quantitative phase analysis. A starting point for the quantitative analysis depends on the direct proportionality between the intensity of the X-ray diffracted by the metal amino acid chelate phase and the amount in the phase mixture. This first step was implemented using calibrations as shown in FIGS. 10 and 11. Integral intensities of the reflections were utilized along with careful preparation and phi-rotation set-up. The limit of detection was stated at a relative error of 1%. Since standards of the metal amino acid chelate was not easily found, a standard sample acting as witness was selected for this determination. For this example, a titanium oxide was selected (rutile polymorph (95%) from Sigma-Aldrich (99% purity)). Mainly reflections of rutile phase did not affect the quantitative determination of the organic metal/minerals analyzed. The RIR (reference intensity ratio) could be employed as a semi-quantitative analysis method as long as RIR values of the structure data is available. The selected routine method was carried out via a multi-phase identification with constituents available as pure phases and a 10% wt. witness material added because a minimum overlap and similar absorption were achieved. From the solid mixture, a calibration curve was obtained under identical XRD set-up conditions as shown in FIG. 10. The background subtraction from a fifth grade polynomial as a baseline was carried out. Cubic spline interpolation may be used instead of polynomial interpolation. Due to this methodology, an absolute calibration method could be assumed and a determination of the content of the solid chelate sample can be related to the direct measurement of intensities. These methods by addition of a known amount of the same phase of interest were controlled by the rutile standard since some evidences of adducts between the metal chelate and the amino acid were found from a solid state and solution reaction in the literature. Results may be compared with the Rietveld method, which is based on theoretical data. This method is based on the minimization of the weighted squares of the deviations between observed and theoretical intensities of the diffractogram. The statistical data obtained for triplicate are shown in FIGS. 16 and 17 for copper and zinc amino acid chelate samples respectively. Based on these results, a high linearity ($R2>0.99$) shows the good accuracy of the method. The analysis of variance (ANOVA) analysis for the compound acting as witness, demonstrated the importance of using this compound as reference for intensity values correction along the X-ray diffraction pattern. From above, the semi quantification of the metal ligates to the amino acid ring—chelate sample—and the free glycine may be directly measured from the calibration curves for solid samples. This procedure was able to differentiate the two polymorphs of glycine, the coordination compounds different to that of chelate sample, the precursors employed from the synthesis reaction and other byproducts that may be present. The above is a key point to track and control major standards for high quality products in the industry. The process as provided herein is not destructive and samples may be kept for further analysis.

Example 2—Liquid Chelate Analysis

A liquid sample was reacted with phytic acid. The reaction between the compounds and the phytic acid was at a pH of 3.0. Phytic acid ionization began via phosphates group in the following order: (a) P1, and P3 at a pH of from about 1.5 to about 2.0; (b) P4 and P6 at a pH of from about 2.0 to about 2.5; (c) P2 and at a pH of about 2.5; and (d) P5 at a pH of from about 3.0 to about 5.0 (see FIGS. 1 and 2). The pKa's were 1, 84, 6, 30, and 9.30 which means that at pH 3.0, the oxygen of the phosphodiester bond were available at this pH and can chelate the metal ion. The order of stability of metal-phytate complexes was found to be Cu>Zn>Co>Mn>Fe>Ca. Even though Ca has one of the lowest affinities for phytate, Calcium was shown to have the greatest impact because calcium is the metal/mineral present at the highest concentration in the diet.

At a pH of about 3.0, one solution of 4.62 g/L of sodium phytate was added to one solution of metal/mineral 0.9% (relation just metal/mineral to complete molecule relation chelate: to ensure Phitate 6:1 or excess of phytate in all cases (Martin C. and Evans W. (1986)). The complex was completely solubilized at a pH of 3.0 (simulating gastric conditions in monogastric animals and gizzard in poultry for example). The pH of this solution was then changed to a pH of about 6.0. The metal/mineral formed homonuclear complexes with phytic acid at a pH of 6.0 which were produced when the source metal/mineral was released by competition with the metal/mineral which was not stabilized by a covalent coordinate bond as a metal amino acid chelate thereby obtaining an abundant precipitate. At a pH of about 6.0 (simulated pH intestinal), the source of metal/mineral was not stable and reacted with phytic acid.

An aliquot of 5 mL of the remainder solution at a pH of 6.0 was taken and passed through an anionic exchange resin. The unreacted phytic acid was eluted with 10 ml of water and the metal amino acid chelate was retained and later eluted with 0.6 M HCL water. Stable unreacted metal amino acid chelate was retained onto the anionic column. The unreacted metal amino acid chelate was then eluted by a 0.6M HCL solution with 6 washes of 5 mL each. The metal amino acid chelate solution was analyzed by HPLC (diodes arranged or mass detector).

The eluted sample was injected by HPLC with three signals obtained (253 or 210 nm range wavelength to detection 200 to 350 nm) at 2.5 min, 3.2 min and 3.5 min retention times). All peaks obtained corresponded to a metal amino acid chelate and free ligand (glycine in this example). The chromatographic setup was based on a HPLC system with a reverse phase C8 column×25 cm. The mobile phase included a mix of the following: methanol (5%), acidic water with formic acid (pH 2.72) (80%) and acetonitrile. The time of analyses was 7 minutes. A peak obtained at 2.5 min was a characteristic signal of a metal amino acid chelate.

I claim:
1. A process for quantifying the amount of unbound metal and bound metal in solution comprising the step of:
   (a) reacting a metal compound with excess phytic acid in an aqueous solution;
   (b) adjusting the pH of the aqueous solution to about 5.0 to about 7.0;
   (c) analyzing an aliquot of the solution from step (b) via high performance liquid chromatography to determine the amount of free ligand and amount of bound metal; and
   (d) analyzing total metal content via an inductively coupled plasma (ICP) technique to determine the total amount of metal present in solution and the amount of any insoluble metal precipitate produced after step (b),
   wherein prior to step (b), the aqueous solution has an initial pH of about 2.0, and
   wherein the metal is selected from the group consisting of Cu, Cr, Zn, Co, Mn, and Ca.
2. The process of claim 1, wherein the bound metal is in the form of a metal amino acid chelate having a molecular weight of less than or equal to 800 daltons (AMU).
3. The process of claim 1, where the pH of the solution in step (b) is adjusted to a pH of about 6.0.
4. A process for quantifying the amount of bound metal amino acid chelate and free ligand in a solid comprising the steps of:
   (a) qualitatively analyzing a solid sample via x-ray crystallography to obtain an x-ray pattern;
   (b) comparing the X-ray pattern of the solid sample from step (a) with one or more x-ray patterns from a reference database;
   (c) determining the amount of bound metal amino acid chelate and free ligand in the solid based on the solid x-ray diffraction intensity, wherein the step of determining amount of bound metal amino acid chelate and free ligand in the solid includes obtaining a calibration curve by:

performing multi-phase identification with a pure phase and a rutile polymorph via x-ray diffraction to obtain a calibration curve; and performing a background subtraction from the calibration curve with a fifth grade polynomial as a baseline.

5. The process of claim 4, wherein the step of comparing the X-ray pattern of the solid sample with x-ray patterns from a reference database, can be followed by a structural refinement process via the Rietveld method.

6. The process of claim 5, wherein the solid is an animal feedstock.

* * * * *